United States Patent [19]

Perrior et al.

[11] Patent Number: 5,149,810

[45] Date of Patent: Sep. 22, 1992

[54] PYRIMIDINE COMPOUNDS

[75] Inventors: Trevor R. Perrior, Wokingham; David J. Tapolczay, Reading; Alan J. Whittle, Twyford, all of Great Britain

[73] Assignee: Imperial Chemical Industries PLC, London, England

[21] Appl. No.: 764,219

[22] Filed: Sep. 23, 1991

Related U.S. Application Data

[63] Continuation of Ser. No. 341,920, Apr. 24, 1989, Pat. No. 5,077,297.

[30] Foreign Application Priority Data

Apr. 22, 1988 [GB] United Kingdom ............... 8809552
Mar. 22, 1989 [GB] United Kingdom ............... 8906329

[51] Int. Cl.$^5$ .................. C07D 239/36; C07D 239/56
[52] U.S. Cl. ................................. 544/309; 544/319; 544/311; 544/312; 544/313
[58] Field of Search .............. 544/309, 311, 313, 319, 544/312

[56] References Cited

U.S. PATENT DOCUMENTS

| | | | |
|---|---|---|---|
| 3,185,689 | 5/1965 | Ruschig et al. | 260/251 |
| 3,235,358 | 2/1966 | Soboczenski | 71/2.5 |
| 3,254,082 | 5/1966 | Loux et al. | 260/260 |
| 3,291,592 | 12/1966 | Evans | 71/2.5 |
| 3,580,913 | 5/1971 | Lutz | 260/260 |
| 3,823,135 | 7/1974 | Pilgram et al. | 260/251 R |
| 3,869,457 | 3/1975 | Lutz et al. | 544/319 |
| 4,145,546 | 3/1979 | Brown et al. | 544/310 |
| 4,147,528 | 4/1979 | McNulty et al. | 71/92 |

FOREIGN PATENT DOCUMENTS

| | | |
|---|---|---|
| 888730 | 12/1971 | Canada . |
| 0129528 | 12/1984 | European Pat. Off. . |
| 0180298 | 5/1986 | European Pat. Off. . |
| 0273409 | 7/1988 | European Pat. Off. . |
| 0338686 | 10/1989 | European Pat. Off. . |
| 1035091 | 7/1966 | United Kingdom . |
| 1035092 | 7/1966 | United Kingdom . |
| 1035097 | 7/1966 | United Kingdom . |
| 1035098 | 7/1966 | United Kingdom . |
| 1447108 | 8/1976 | United Kingdom . |
| 2130214 | 5/1984 | United Kingdom . |

OTHER PUBLICATIONS

Khromov-Borison, Chemical Abstracts, vol. 61:4345h (1964).
Kloetzer, Chemical Abstracts, vol. 64:3529c (1966).
Danek et al.; Chemical Abstracts, vol. 73:12826n (1970).
Byard et al., Chemical Abstracts, vol. 110:95152c (1989).
Luethy, Chemical Abstracts, vol. 102:45969d (1985).
Ashani et al.; Chemical Abstracts, vol. 64:2084f (1966).
Isbecque et al.; Chemical Abstracts, vol. 54:560i (1960).
Giner-Sorolla et al.; Chemical Abstract, vol. 53:9234h (1959).
Bergmann et al.; Chemical Abstracts, vol. 54:6736; (1960).
Chemical Abstracts, vol. 105, No. 23, Dec. 8, 1986, p. 566, Abstract No. 2208595s, Columbia, Ohio, US; & JP-A-61 083 146 (Nippon Soda Co., Ltd.) Apr. 16, 1986.

Primary Examiner—John M. Ford
Attorney, Agent, or Firm—Cushman, Darby & Cushman

[57] ABSTRACT

A pyrimidinone compound of formula (IIIA) or (VA):

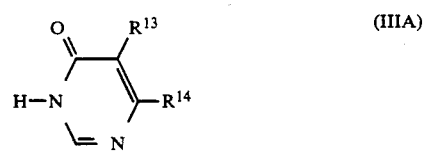

wherein $R^{13}$ is hydrogen, halogen or cyano and $R^{14}$ is halo or haloalkyl with the proviso that (a) when $R^{13}$ is cyano, $R^{14}$ is other than chlorine; (b) $R^{13}$ and $R^{14}$ are not both halo; (c) when $R^{13}$ is halo $R^{14}$ is other than monofluoromethyl; and (d) when $R^{13}$ is hydrogen $R^{14}$ is not halo or a halomethyl group;

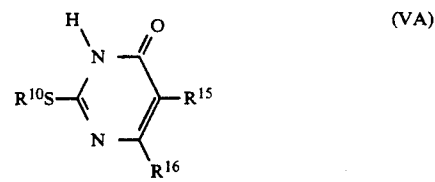

wherein $R^{10}$ is hydrogen or $C_{1-4}$alkyl; $R^{15}$ is cyano and $R^{16}$ is $R^6$ is defined in relation to formula (V) or $R^{15}$ is hydrogen or halogen other than fluorine and $R^{16}$ is pentafluoroethyl or difluoromethyl. These compounds are useful as intermediates in the preparation of insecticidal compounds.

3 Claims, No Drawings

PYRIMIDINE COMPOUNDS

The present invention relates to novel phenyl pyrimidinone derivatives which have insecticidal activity, to processes for their preparation and to their use as insecticides.

Canadian Patent No 888730 discloses certain herbicidal compounds of formula:

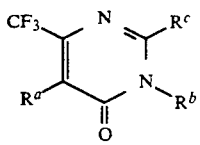

Where $R^a$ is inter alia halo or nitro; $R^b$ is inter alia optionally substituted phenyl and $R^c$ is inter alia hydrogen. However no specific examples of substituted phenyl groups $R^b$ are disclosed.

According to the present invention there is provided a compound of formula (I)

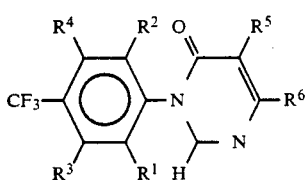

wherein $R^1$ and $R^2$ are independently selected from halogen or nitro; $R^3$ and $R^4$ are independently selected from hydrogen or halogen; $R^5$ is hydrogen, halogen or cyano; and $R^6$ is halogen or haloalkyl; provided that $R^1$, $R^2$, $R^3$ and $R^4$ are not all fluorine.

Suitable halogen groups for $R^1$, $R^2$, $R^3$, $R^4$, $R^5$ and $R^6$ include fluoro, chloro, bromo or iodo.

Preferably at least one of $R^1$ or $R^2$ is halo. In particular $R^1$ and $R^2$ are both fluoro or chloro.

Suitably $R^3$ and $R^4$ are hydrogen.

In preferred embodiments $R^1$, $R^2$, $R^3$ and $R^4$ are not all halo.

Suitably $R^5$ is hydrogen or halogen. Most preferably $R^5$ is hydrogen, chlorine, or bromine.

Suitable haloalkyl groups $R^6$ contain straight or branched chain alkyl groups suitably having from 1 to 6 carbon atoms. Particular haloalkyl groups are di- or trihalomethyl groups, such as trifluoromethyl or difluoromethyl or pentahaloethyl groups such as pentafluoroethyl.

A preferred sub-groups of compounds of formula (I) are compounds of formula (IA)

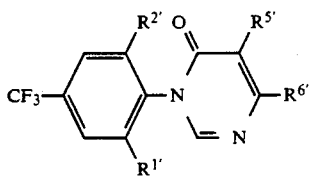

where one of $R^{1'}$ or $R^{2'}$ is halo and the other is halo in particular fluorine, chlorine or bromine or nitro; $R^{5'}$ is hydrogen or halogen in particular chlorine or bromine; and $R^{6'}$ is trifluoromethyl or pentafluoroethyl.

Examples of compounds of formula (I) are set out in Table I below.

TABLE I

| COMPOUND NO. | $R^1$ | $R^2$ | $R^3$ | $R^4$ | $R^5$ | $R^6$ |
|---|---|---|---|---|---|---|
| 1 | Cl | Cl | H | H | H | $CF_3$ |
| 2 | Cl | $NO_2$ | H | H | H | $CF_3$ |
| 3 | $NO_2$ | $NO_2$ | H | H | H | $CF_3$ |
| 4 | F | Cl | H | H | H | $CF_3$ |
| 5 | Br | Cl | H | H | H | $CF_3$ |
| 6 | Br | Br | H | H | H | $CF_3$ |
| 7 | Cl | $NO_2$ | H | H | F | $CF_3$ |
| 8 | Cl | $NO_2$ | H | H | Br | $CF_3$ |
| 9 | Cl | Cl | H | H | Br | $CF_3$ |
| 10 | Cl | I | H | H | H | $CF_3$ |
| 11 | F | F | H | H | H | $CF_3$ |
| 12 | Cl | $NO_2$ | H | H | Cl | $CF_3$ |
| 13 | Cl | Cl | H | H | Cl | $CF_3$ |
| 14 | Cl | $NO_2$ | H | H | I | $CF_3$ |
| 15 | $NO_2$ | $NO_2$ | H | H | Br | $CF_3$ |
| 16 | $NO_2$ | $NO_2$ | Cl | H | H | $CF_3$ |
| 17 | Cl | $NO_2$ | H | H | H | $C_2F_5$ |
| 18 | Cl | Cl | H | H | H | $C_2F_5$ |
| 19 | F | Cl | H | H | Br | $CF_3$ |
| 20 | F | $NO_2$ | H | H | H | $CF_3$ |
| 21 | $NO_2$ | Br | H | H | H | $CF_3$ |
| 22 | F | Cl | H | H | Cl | $CF_3$ |
| 23 | F | F | H | H | Br | $CF_3$ |
| 24 | $NO_2$ | $NO_2$ | H | H | Cl | $CF_3$ |
| 25 | Br | $NO_2$ | H | H | Cl | $CF_3$ |
| 26 | Br | $NO_2$ | H | H | Br | $CF_3$ |
| 27 | Cl | $NO_2$ | H | H | CN | $CF_3$ |
| 28 | Cl | Cl | H | H | CN | $CF_3$ |
| 29 | Cl | $NO_2$ | H | H | Br | $C_2F_5$ |
| 30 | Cl | Br | H | H | Br | $CF_3$ |
| 31 | Br | Br | H | H | Cl | $CF_3$ |
| 32 | Br | Br | H | H | Br | $CF_3$ |
| 33 | Cl | Cl | H | H | Br | $C_2F_5$ |
| 34 | Cl | Br | H | H | Cl | $CF_3$ |
| 35 | Cl | Cl | H | H | H | Cl |
| 36 | Cl | $NO_2$ | H | H | H | Cl |
| 37 | Cl | $NO_2$ | H | H | Cl | $C_2F_5$ |
| 38 | F | Cl | H | H | H | $C_2F_5$ |
| 39 | F | F | H | H | Cl | $C_2F_5$ |
| 40 | F | Cl | H | H | Br | $C_2F_5$ |
| 41 | Cl | $NO_2$ | H | H | H | $CF_2H$ |
| 42 | Cl | Br | H | H | H | $C_2F_5$ |
| 43 | Cl | Br | H | H | Br | $C_2F_5$ |
| 44 | Br | $NO_2$ | H | H | H | $C_2F_5$ |
| 45 | Br | Br | H | H | H | $C_2F_5$ |
| 46 | Cl | Cl | H | H | Cl | $C_2F_5$ |
| 47 | Br | Br | H | H | Br | $C_2F_5$ |

Compounds of formula (I) can be prepared by reacting a compound of formula (II)

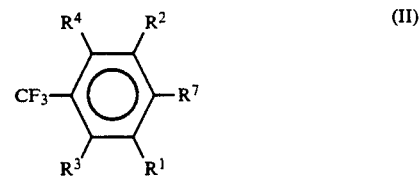

wherein $R^1$, $R^2$, $R^3$ and $R^4$ are as defined in relation to formula (I) and $R^7$ is a leaving group; with a compound of formula (III)

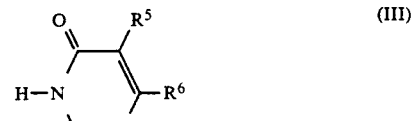

wherein $R^5$ and $R^6$ are as defined in relation to formula (I); and thereafter if desired carrying out one or more of the following steps: (i) converting the group $R^5$ where it is hydrogen, to different group $R^5$; or (ii) converting a group $R^1$, $R^2$, $R^3$ or $R^4$ to a different such group.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, an alcohol or an aprotic polar solvent such as dimethylformamide or dimethylacetamide.

Suitable leaving groups $R^7$ include halo groups such as fluoro, chloro, bromo or iodo.

If necessary an appropriate catalyst such as a crown ether or copper can be added depending upon the precise nature of $R^7$. Further details of the processes for preparation of the compounds may be ascertained from the Examples set out hereinafter.

Conversion of the group $R^5$ from hydrogen into a halogen group such as bromine or chloro as in optional step (i) above can be carried out by reacting the compound of formula (I) where $R^5$ is hydrogen with a halogen such as bromine in the presence of a base such as sodium acetate. The reaction is suitably carried out in an organic solvent such as acetic acid at moderate temperatures of from 0°–50° C., conveniently at ambient temperature.

Alternatively the conversion can be carried out using other known halogenating agents such as N-bromosuccinimide or N-chlorosuccinimide in an organic solvent such as acetonitrile or dimethylformamide. Suitably elevated temperatures of from 60° to 100 °C. are employed.

Optional step (ii) above may also be carried out by conventional means. For example compounds of formula (I) wherein $R^1$ and/or $R^2$ is nitro can be converted to the corresponding compound of formula (I) wherein $R^1$ and/or $R^2$ is halo by reduction of the nitro groups to an amino group to form a compound of formula (IV):

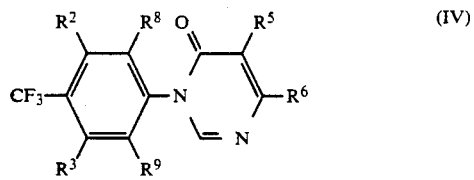

(IV)

wherein $R^3$, $R^4$, $R^5$ and $R^6$ are as defined in relation to formula (I) and $R^8$ and $R^9$ are amino or a group $R^1$ or $R^2$ as defined in relation to formula (I) provided that at least one of $R^8$ or $R^9$ is amino; and thereafter converting the amino group $R^8$ and/or $R^9$ to halo.

Compounds of formula (IV) are novel and as such form a further aspect of the invention.

Reduction of the nitro groups to form a compound of formula (IV) can be carried out by reacting the compound with a reducing agent such as stannous chloride in acid conditions, for example in a solution in concentrated hydrochloride acid. Moderate temperatures of from 2° to 45 °C. are suitably employed.

Subsequent halogenation may be carried out by reaction with t-butylnitrite and a copper halide salt such as copper (I)iodide. This step is suitably carried out in an organic solvent such as acetonitrile at low temperatures of from −20° to +20° C. preferably at about 0° C.

Compounds of formula (III) can be prepared by reacting a compound of formula (V)

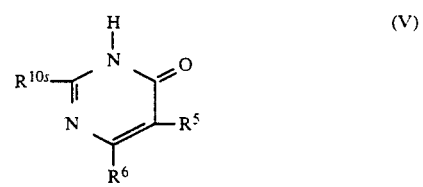

(V)

wherein $R^{10}$ is hydrogen or $C_{1-4}$ alkyl such as ethyl with Raney Nickel in an appropriate solvent such as aqueous ammonia.

Compounds of formula (V) are either known compounds or they can be prepared from known compounds by known methods (see for example A Giner-Sorolla, A Bendick: J. Am. Chem, Soc, 1958, 80, 5744).

Some compounds of formula III), (III) and (V) are novel and these form a further aspect of the invention. Therefore further according to the present invention there is provided a compound of formula (IIA)

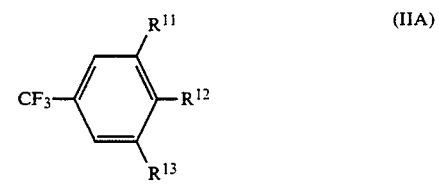

(IIA)

wherein $R^{11}$ is chlorine, $R^{12}$ is fluorine and $R^{13}$ is iodine, or $R^{11}$ is nitro, $R^{12}$ is bromo and $R^{13}$ is bromo.

The compound of formula (IIA) where $R^{11}$ is chlorine, $R^{12}$ is fluorine and $R^{13}$ is iodine can be prepared from the compound of formula (II) where $R^1$ is chlorine, $R^2$ is nitro, $R^7$ is fluorine and $R^3$ and $R^4$ are hydrogen by reduction of the group $R^2$ to amino and subsequent halogenating to the desired compound of formula IIA using methods analogous to those described above in relation to optional step (ii) for the preparation of the compounds of formula (I).

The intermediate compound of formula (VI):

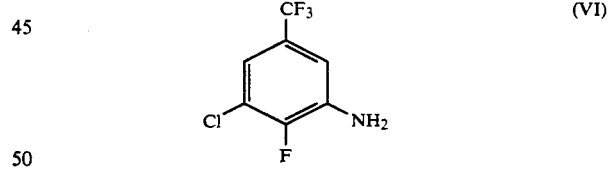

(VI)

is novel and forms a further aspect of the invention.

Novel compounds of formula (III) are compounds of formula (IIIA)

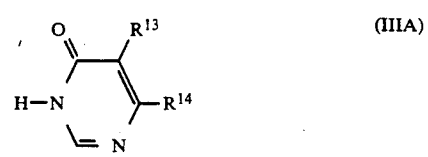

(IIIA)

wherein $R^{13}$ is hydrogen, halogen or cyano and $R^{14}$ is halo or haloalkyl with the proviso that (a) when $R^{13}$ is cyano, $R^{14}$ is other than chlorine; (b) $R^{13}$ and $R^{14}$ are not both halo; (c) when $R^{13}$ is halo, $R^{14}$ is other than monofluoromethyl; and (d) when $R^{13}$ is hydrogen, $R^{14}$ is not halo or a halomethyl group.

A particular example of $R^{14}$ is pentafluoroethyl.

Compounds of formula (IIIA) can be prepared by various routes including preparation from the appropriate compound of formula (V) as described above. Alternatively the compound of formula (IIIA) can be prepared from the appropriate compound of formula (III) where $R^5$ is hydrogen by halogenation using for example conditions similar to those described above in relation to the conversion of $R^5$ from hydrogen to halogen. Compounds of formula (IIIA) where $R^{13}$ is cyano can be prepared by reacting a compound of formula (III) where $R^5$ is bromine with a cyanide salt such as copper (I) cyanide in an organic solvent such as quinoline at elevated temperature of from 200° to 250 °C.

Novel compounds of formula (V) are compounds of formula (VA):

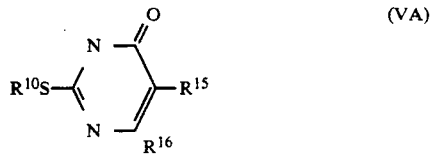

wherein $R^{10}$ is as defined in relation to formula (V), $R^{15}$ is cyano and $R^{16}$ is $R^6$ as defined in relation to formula (V) or $R^{15}$ is hydrogen or halogen other than fluorine and $R^{16}$ is pentafluoroethyl or difluoromethyl.

Compounds of formula (VA) can be prepared by reacting a compound of formula (VII):

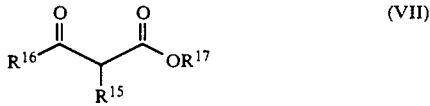

wherein $R^{15}$ and $R^{16}$ are as defined in relation to formula (VA) and $R^{17}$ is a $C_{1-6}$ alkyl group with thiourea or an appropriate alkylated derivative thereof in the presence of a strong base such as an alkali metal alkoxide such as sodium methoxide. Elevated temperatures of from 60 °C. to 90 °C. are suitably employed.

Other compounds of formula (II), (III) and (V) and compounds of formula (VII) are either known compounds or they can be prepared from known compounds by conventional methods.

The compounds of formula (I) may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals.

Compounds of formula (I) are particularly useful against public health pests such as cockroaches and houseflies.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium liqnosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000q/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components. The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lamdacyhalothrin, biphenthrin, fenpropathrin, cyfluthrin, tefluthrin, fish safe pyrethroids for example etofenprox, natural pyrethrin, tetramethrin, s-bioallethrin, fenfluthrin, prallethrin and 5-benzyl-3-furylmethyl-(E) -(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphos-methyl, fenitrothion or diazionon;

c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;

d) Benzoyl ureas such as triflumeron, or chlorofluazuron;

e) Organic tin compounds such as cyhexatin, fenbutatin oxide, azocyclotin;

f) Macrolides such as avermectins or milbemyins, for example such as avamectin, avermectin, and milbemycin;

g) Hormones such as pheromones;

h) Organochlorine compounds such as benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamax, and dodecyl imidazole.

Suitable herbicides, fungicides and plant-growth regulators for inclusion in the compositions will depend upon the intended target and the effect required. An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The compounds of formula I and compositions comprising them have shown themselves active against a variety of insect and other invertebrate pests. They are particularly useful in controlling public health pests such as flies and cockroaches. They may also be active against organophosphates and pyrethroid resistant strains of pests such as houseflies (*Musca domestica*). They may be effective in combating both susceptible and resistant strains of the pests in their adult, larval and intermediate staqes of growth, and may be applied to the infested host animal by topical, oral or parenteral administration.

The following Preparations and Examples are given by way of illustration.

PREPARATION 1

This description illustrates the preparation of 4-pentafluoroethyl-2-thiouracil.

Thiourea (3 g) was added to a solution of sodium methoxide in methanol (previously prepared by adding sodium metal (1.089) to dry methanol (20 ml)). This was followed by ethyl pentafluoropropionyl acetate (9.61 g) and the reaction mixture was heated under reflux for 3 days. After cooling the solvent was evaporated, in vacuo. to qive a brown solid, which was acidified with dilute aqueous hydrochloric acid and extracted with diethyl ether. The combined organic extracts were dried, and removal of the solvent by evaporation, under reduced pressure, gave 4-pentafluoroethyl-2-thiouracil (4.14 g), which was immediately carried to the next stage;

$^1$H NMR $\delta$(CDCl$_3$) 12.3(1H, brs), 11.65 (1H, brs) and 6.2(1H,s).

PREPARATION 2

This description illustrates the preparation of 4-pentafluoroethylpyrimidin-6-one.

Raney Nickel (0.83 g, of a 50% dispersion in water) was added to a suspension of 4-pentafluoroethyl-2-thiouracil (0.5 g) in a mixture of concentrated aqueous ammonia (0.23 ml) in water (6 ml). The reaction mixture was heated to reflux for 5.5 hours, cooled, stood overnight, and filtered hot through hyflo. The filtrate was concentrated by evaporation of the solvent under reduced pressure to give the desired compound as a pale green solid. Sublimation (100° C., 0.1 mbar) gave 4-pentafluoroethylpyrimidin-6-one as a white solid mpt 122°–126° C.;

'H NMR δ(CDCl₃) 13.05 (1H, brs) 8.30 (1H,s) and 6.94 (1H,s).

PREPARATION 3

This description illustrates the preparation of 5-bromo-4-trifluoromethylpyrimidin-6-one.

Bromine (4.62 g) was added in one portion to a stirred solution of 4-trifluoromethylpyrimidin-6-one (4.3 g) and sodium acetate (10.53 g) in acetic acid (43 ml). After stirring for 2 hours, the reaction mixture was left to stand for a period of 3 days, after which time it was heated to 80° C. for 1 hour. After cooling to the ambient temperature (ca 22° C.), the solvent was evaporated under reduced pressure. The resultant orange solid was dissolved in ethyl acetate, and washed several times with water. The combined aqueous washings were extracted with ethylacetate, and the combined organic layers were washed with aqueous sodium thiosulphate solution, followed by aqueous sodium bicarbonate solution and brine. After drying over magnesium sulphate, evaporation of the solvent under reduced pressure gave 5-bromo-4-trifuoromethylpyrimidin-6-one as a white solid (4.8 g, mpt 226°–227° C.);

'H NMRδ(CDCl₃), 8.05(s); ¹⁹F NMR δ(CDCl₃), −67.4(s).

PREPARATION 4

This description illustrates the preparation of 5-iodo-4-trifluoromethylpyrimidin-6-one.

N-Iodosuccinimide (2.75 g) was added to a stirred suspension of 4-trifluoromethylpyrimidin-6-one (1 g) in dry acetonitril (13 ml). The reaction mixture was stirred at the ambient temperature for 2 hours, and then heated under reflux for 10 hours. After cooling, removal of the solvent under reduced pressure gave a brown solid which was recrystallised from water to give 5-iodo-4-trifluoromethylpyrimidin-6-one as a pale orange solid (150 mg);

'H NMRδ(CDCl₃+3 drops DMSO) 13.5 (1H, brs) and 8.00 (1H,s).

PREPARATION 5

This description illustrates the preparation of 5-chloro-4-trifluoromethylpyrimidin-6-one.

N-chlorosuccinimide (6.56 g) was added to a stirred suspension of 4-trifluoromethylpyrimidin-6 -one (4 g) in dry acetonitrile (50 ml), and the mixture heated under reflux for 17 hours. After cooling, the the solvent was removed by evaporation under reduced pressure to qive a white solid which was recrystallised from water (twice) to qive 5-chloro-4-trifluoromethylpyrimidin-6-one as a white solid (1.06 g, mpt 191°–192° C.)

'H NMR δ(CDCl₃+1 drop DMSO) 13.5 (1H, brs) and 8.05 (1H, d).

PREPARATION 6

This description illustrates the preparation of 5-cyano-4-trifluoromethylpyrimidin-6-one.

Copper(I)cyanide (80 mg) was added to a solution of 5-bromo-4-trifluoromethylpyrimidin-6-one (150 mg) in quinoline (5 ml). The reaction mixture was then heated to the reflux temperature for a period of 3 hours. After cooling to the ambient temperature, the reaction mixture was poured into dilute aqueous acetic acid, and extracted into ethyl acetate. After drying, evaporation of the solvent under reduced pressure gave a brown oil, which was subjected to chromatography on silica gel plates using ethylacetate containing acetic acid and water (250:5:1 by volume) as eluent. The desired fraction was collected, and the brown solid thus isolated was identified as a phenolic salt. This material was dissolved in ethanol, and acidified with ethanolic hydrogen chloride. Evaporation of the solvent under reduced pressure gave a brown solid which was dissolved in diethyl ether and filtered. Evaporation of the solvent under reduced pressure gave 5-cyano-4-trifluoromethyl-pyrimidin-6-one as a brown solid. IR (Nujol mull) 3100, 2920, 2235, 1730, 1700, 1680, 1600, 1440, 1330, 1210, 1160, 1130 and 958 cm⁻;

'H NMR δ(DMSO) 8.70 (1H,s), 3.45 (1H, brs).

Preparation 7

This description illustrates the preparation of 3,4-difluoro-5-nitrotrifluoromethylbenzene.

A mixture of 4-chloro-3,5-dinitrotrifluoromethylbenzene (10 g) and dry potassium fluoride (4.3 g) in dry dimethylformamide (25 ml) was stirred vigorously and heated to 100° C. for 16 hours. After cooling to ambient temperature, further potassium fluoride (2.15 g) was added, and the mixture was heated to 130° C. for 2 days. After cooling, the reaction mixture was poured into water, and extracted with diethyl ether. The organic layer was dried, filtered, and the solvent removed by evaporation, under reduced pressure. The residual oil was subjected to kugelrohr distillation under reduced pressure to qive 3,4-difluoro-5nitrotrifluoromethylbenzene containing dimethylformamide as a yellow oil, as the first distilling component (0.18 g);

'H NMR δ(CDCl₃) 8.2 (1H, m) and 7.83 (1H, m).

Preparation 8

This description illustrates the preparation of 3-amino-5-chloro-4-fluorotrifluoromethylbenzene.

5-Chloro-4-fluoro-3-nitrotrifluoromethylbenzene (50 g) was added to a cooled (5° C.) solution of stannous chloride (140 g) in concentrated aqueous hydrochloric acid (187 ml). After stirring for several hours at the ambient temperature (ca 22° C.), the reaction mixture was stood overnight. After basification by the addition of sodium hydroxide, the reaction mixture was extracted with ethyl acetate. The organic layer was washed with water, dried, and the solvent removed by evaporation under reduced pressure. The residual yellow oil was kuqelrohr distilled under reduced pressure to qive 3-amino-5-chloro-4-fluorotrifluoromethylbenzene (32 g):bp. 105° C./11 mm Hg;

'H NMR δ(CDCl₃) 7.03 (1H, dq), 6.90 (1H, dq).

Preparation 9

This description illustrates the preparation of 3-chloro-4-fluoro-5-iodotrifluoromethylbenzene.

3-Amino-5-chloro-4-fluorotrifluoromethylbenzene (10 g) was added dropwise to a stirred suspension of t-butylnitrite (25 g) and copper (I) iodide (9 g) in dry acetonitrile (185 ml) whilst the temperature was maintained at 0° C. After the addition was complete the stirred reaction mixture was kept at 0° C. for a further 2 hours, after which it was allowed to warm to ambient temperature. After the addition of dilute aqueous hydrochloric acid, the reaction mixture was extracted into ether, the organic layer thoroughly washed with aqueous sodium metabisulphite solution, and dried over anhydrous magnesium sulphate. Removal of the solvent by evaporation under reduced pressure gave a brown oil, which was purified by chromatography on silica gel with a mixture of 5% ethyl acetate (by volume) in n- hexane as eluent. The first eluting component was collected to give 3-chloro-4-fluoro-5-iodotrifluoromethylbenzene as a pale yellow oil (5.66 g);

'H NMR δ(CDCl₃) 7.8 (1H, m) and 7.65 (1H, m); ¹⁹F NMR δ(CDCl₃)−63.96 (3F, s) and −89.48 (1F, s).

Preparation 10

The following compound was prepared according to the general method of Preparation 3 from appropriate compounds of formula (III).

5-Bromo-4-pentafluoroethylpyrimidin-6-one (mp. 165°–166.5° C.);

'H NMR δ(CDCl₃) 13.6 (1H, brs) and 8.35 (1H, s).

Preparation 11

This description illustrates the preparation of 5-chloro-4-pentafluoroethylpyrimidin-6-one.

A solution of 4-pentafluoroethylpyrimidin-6-one (0.4 g) and N-chlorosuccinimide (0.27 g) in dry dimethylformamide (5 ml) was heated to 80° C. for 3 hours. After cooling to ambient temperature, the reaction mixture was poured into water, and extracted into ethyl acetate. The organic layer was dried, over anhydrous maqnesium sulphate, filtered, and evaporation of the solvent under reduced pressure gave a brown oil. Recrystallisation from water gave 5-chloro-4-pentafluoroethylpyrimidin-6-one 'H NMR δ(CDCl₃) 8.22 (s).

Preparation 12

This description illustrated the preparation of 4-difluoromethylpyrimidin-6-one.

Thiourea was reacted with chloro-difluoro acetoacetate in the presence of sodium methoxide according to the manner illustrated in Preparation 1. The crude material so formed was then reacted with Raney nickel according to the manner illustrated in Preparation 2. The orange product so formed was identified as a mixture of components, containing 75% (by G.L.C. analysis) of 4-difluoromethylpyrimidin-6-one.

'H NMR δ(CDCl₃+1 drop DMSO) 8.10 (1H, s), 6.70 (1H, s) and 6.38 (1H, t).

This material was used without further purification.

Preparation 13

This description illustrated the preparation of 3,4-dibromo-5-nitrotrifluoromethylbenzene.

4-Amino-3-bromo-5-nitrotrifluoromethylbenzene (10 g) in acetonitrile (7 ml) was added dropwise to a stirred suspension of t-butylnitrite (18.6 g) and copper (II) bromide (10 g) in dry acetonitrile (138 ml) whilst the temperature was maintained at 0° C. After the addition was complete the stirred reaction mixture was kept at 0° C. for a further 2 hours, after which time it was allowed to warm to ambient temperature. The reaction mixture was poured into dilute aqueous hydrochloric acid and extracted into diethyl ether. The organic layer was thoroughly washed with water and brine and dried over anhydrous magnesium sulphate. Filtration and evaporation of the solvent under reduced pressure gave a yellow oil which was subjected to kuqelrohr distillation to give 3,4-dibromo-5-nitrotrifluoromethylbenzene as a yellow oil, which solidified on cooling. B.p. 140° C. at 15 mm Hg).

'H NMR δ(CDCl₃) 8.10 (1H, d

EXAMPLE 1

This Example illustrates the preparation of 1-(2,6-dichloro-4-trifluoromethyl)-4-trifluoromethyl-pyrimidin-6-one (Compound 1 in Table I).

A dry reaction flask was purged with nitrogen and charged with a 50% suspension of sodium hydride (1.6 g). The sodium hydride was washed with pentane and suspended in dimethylformamide (0MF, 20 ml). A solution of 6-trifluoromethylpyrimidin-4-one (5 g) in DMF (30 ml) was added dropwise. When the addition was complete the reaction was stirred for a further fifteen minutes, then 3,5-dichloro-4-fluorobenzotrifluoride (28 g) was added in one portion and the mixture heated at 100° C. for six hours. The reaction mixture was allowed to cool, poured into brine, and extracted with ethyl acetate. The organic layer was washed with brine, dried over maqnesium sulphate and evaporated in vacuo to qive a brown residue which was purified by chromatography on silica gel using 20% diethyl ether/petrol as eluent to qive (compound 1 in Table I) (812 mg). 'H NMR δ(CDCl₃) 8.0 (1H,s), 7.8 (2H,s), 7.0 (1H,s).

EXAMPLE 2

The following compounds were prepared according to the general method of Example 1 from appropriate compounds of formula II and formula III.

(a) 1-(2-Chloro-6-nitro-4-trifuoromethylphenyl)-4-trifluoromethylpyrimidin-6-one (Compound 2 in Table I) mp. 149°–150° C.;

'H NMR: δ(CDCl₃) 8.4 (1H,m), 8.2 (1H,m), 8.1 (1H,s), 7.0 (1H,s).

(b) 1-(2-Fluoro-6-chloro-4-trifluoromethylphenyl)-4-trifluoromethylpyrimidin-6-one (Compound 4 in Table I).

'H NMR: δ(CDCl₃) 8.08 (1H, s), 7.74 (1H, s), 7.55 (1H, d), 6.98 (1H, s).

(c) 1-(2-Bromo-6-chloro-4-trifluoromethylphenyl)-4-trifluoromethylpyrimidin-6-one (Compound 5 in Table 1. mp. 172°–174.8° C.;

'H NMR: δ(CDCl₃) 8.03 (1H, s), 7.99 (1H, s), 7.84 (1H, s), 7.00 (1H, s).

(d) 1-(2,6-Dibromo-4-trifluromethylphenyl)-4-trifluoromethylpyrimidin-6-one (Compound 6 in Table I) mp. 177.6°–179.8° C.

NMR: δ(CDCl₃) 8.08 (2H, s), 7.98 (1H, s) 7.00 (1H, s).

(e) 1-(2-Chloro-4-trifluoromethyl-6-nitrophenyl)4-pentafluoroethylpyrimidin-6-one (Compound no 17 in Table I); except that the reaction was heated to 100° C. for 4 hours. The compound showed a mp. 145°–146.5° C.;

'H NMR δ(CDCl₃) 8.45 (1H, s) 8.21 (1H,s), 8.11 (1H, s) and 7.02 (1H, s).

(f) 1-(2,6-Dichloro-4-trifluoromethylphenyl)-4-pentafluoroethylpyrimidin-6-one (Compound 18 in Table I); except that the reaction was heated to 100° C. for 16 hours. The compound showed mp. 168.7°–169.8° C.;

'H NMR δ(CDCl₃) 8.00 (1H, s), 7.82 (2H, s) and 7.05 (1H, s).

(g) 1-(2,6-Difluoro-4-trifluoromethylphenyl)-4-trifluoromethylpyrimidin-6-one (Compound 11 in Table I); except that a four fold excess of aryl fluoride was used, and the reaction mixture was heated at 90° C. for 36 hours.

'H NMR δ(CDCl₃) 8.12 (1H, s), 7.48 (2H, d) and 6.98 (1H,s).

(h) 1-(2-Chloro-6-iodo-4-trifluoromethylphenyl) 4-trifluoromethylpyrimidin-6-one (Compound 10 in Table I); except that the reaction was heated to 90° C. for 16 hours.

'H NMR δ(CDCl$_3$) 8.15 (s, 1H), 7.95 (s, 1H), 7.85 (s, 1H) and 7.0 (s, 1H); $^{19}$F NMRδ(CDCl$_3$) −63.6 (3F, s) and −72.0 (3F, s).

(i) 1-(2-Fluoro-6-nitro-4-trifluoromethylphenyl) -4-trifluoromethylpyrimidin-6-one (Compound 20 in Table I); except that the reaction mixture was maintained at the ambient temperature for 2 hours. The compound showed mp. 147°-151° C.

'H NMR δ(CDCl$_3$) 8.38 (1H, s), 8.37 (1H, s); 7.97 1H, d) and 6.98 (1H, s).

(j) 1-(2-Bromo-6-nitro-4-trifluoromethylphenyl) -4-trifluoromethylpyrimidin-6-one (Compound 21 in Table I); except that the reaction was heated at 75° C. for 16 hours. The compound showed mp. 128°-130° C.

'H NMR δ(CDCl$_3$) 8.45 (1H, d), 8.35 (1H, d), 8.10 (1H, s) and 6.95 (1H, s). In this Example R$^7$ in formula (II) represents bromine.

(k) 1-(2,6-Dichloro-4-trifluoromethylphenyl)-5-bromo-4-trifluoromethylpyrimidin-6-one (Compound 9 in Table I); except that the reaction mixture was heated 75° C. for 6 hours, followed by heating at 90° C. for 24 hours. The compound showed mp. 167°-168° C.

'H NMR δ(CDCl$_3$) 7.95 (1H, s) and 7.82 (2H, s); $^{19}$F NMR δ(CDCl$_3$) −63.80 (3F, s) and −67.45 (3F, s).

(l) 1-(2,6-Dinitro-4-trifluoromethylphenyl)-5-bromo-4-trifluoromethylpyrimidin-6-one (Compound 15 in Table I); except that the reaction mixture was maintained at ambient temperature for 16 hours. The compound showed mp. 199.5°-202° C.

H NMR δ(CDCl$_3$) 8.8 (2H, s) and 8 45 (1H, s).

(m) 1-(2,Chloro-6-nitro-4-trifluoromethyl)-5-chloro-4-trifluoromethylpyrimidin-6-one (compound 12 in Table I); except that the reaction mixture was stirred at the ambient temperature for 2 hours. The compound showed mp 145°-147° C.

'H NMR CDCl$_3$) 8.5 (1H, s), 8.25 (1H, s) and 8.2 (1H, s).

(n) 1-(2,6-dichloro-4-trifluoromethyl)-5-chloro- 4-trifluoromethylpyrimidin-6-one (Compound 13 in Table I); except that the reaction mixture was heated at 85° C. for a period of 20 hours. The compound showed mp. 166°-168° C.

'H NMR δ(CDCl$_3$) 7.95 (1H, s) and 7.85 (2H, s).

(o) 1-(2-bromo-6-nitro-4-trifluoromethylphenyl)-5-chloro-4-trifluoromethylpyrimidin-6-one (compound 25 in Table I); except that the reaction mixture was heated to 90° C. for 5 hours. The compound showed mp. 136.5°-138° C.

'H NMR δ(CDCl$_3$) 8.50 (1H, s), 8.38 (1H, s) and 8.02 (1H, s). In this example R$^7$ in formula (II) represents bromine.

(p) 1-(2-chloro-6-fluoro-4-trifluoromethylphenyl) -5-chloro-4-trifluoromethylpyrimidin-6-one (compound 22 in Table I); except that the reaction mixture was heated to 90° C. for 40 hours.

'H NMR δ(CDCl$_3$) 8.98 (1H, s), 7.74 (1H, s) and 5.57 (1H, d).

(q) 1-(2-Bromo-6-chloro-4-trifluoromethyl)-5-chloro-4-trifluoromethylpyrimidin-6-one (Compound 34 in Table I).

'H NMR δ(CDCl$_3$) 8.00 (1H, s), 7.93 (1H, s), 7.88 (1H, s).

(r) 1-(2,6-Dibromo-4-trifluoromethyl)-5-chloro-4-trifluoromethylpyrimidin-6-one (Compound 31 in Table I); except that the reaction was heated at 90° C. for 16 hours. The compound showed mp. 160°-161° C.

'H NMR δ(CDCl$_3$) 8.03 (2H, s), 7.91 (1H, s), (s) 1-(2-Bromo-6-chloro-4-trifluoromethyl)-5-bromo-4-trifluoromethylpyrimidin-6-one (Compound 30 in Table I); except that the reaction mixture was heated to 85° C. for 16 hours. The compound showed mp. 166°-168° C.

'H NMR δ(CDCl$_3$) 7.98 (1H, s), 7.92 (1H, s), 7.88 (1H, s).

(t) 1-(2-Chloro-6-nitro-4-trifluoromethyl)-5-cyano-4-trifluoromethylpyrimidi-6-one (compound 27 in Table I); except that the reaction mixture was maintained at the ambient temperature for 18 hours. The compound showed mp. 168.7°-169.2° C.

'H NMR δ(CDCl$_3$) 8.50 (1H, d) 8.26 (1H, s), 8.24 (1H, d).

(u) 1-(2,6-Dichloro-4-trifluoromethyl)-5-cyano-4-trifluoromethylpyrimidin-6-one (Compound 28 in Table I); except that the reaction mixture was heated to 100° C. for 23 hours.

'H MMR δ(CDC;$_3$) 8.19 (1H, s), 7.85 (2H, s).

(v) 1-(2,6-dichloro-4-trimethylfluorophenyl)-4-chloropyrimidin-6-one (compound 35 in Table 1); except that the reaction mixture was heated to 90° C. for 27 hours. The compound showed mp. 119.1°-122° C.

'H NMR δ(CDCl$_3$) 7.84 (1H, s); 7.80 (2H, s) and 6.7 (1H, s).

(w) 1-(2-chloro-6-fluoro-4-trifluoromethylphenyl)-4-pentafluoroethylpyrimidin-6-one (compound 38 in Table I); except that the reaction was heated to 90° C. for 23 hours and a four fold excess of the aryl fluoride was used. The compound showed mp. 121°-122.8° C.

'H NMR δ(CDC;$_3$) 8.05 (1H, S), 7.75 (1H, s), 7.58 (1H, dd) and 7.06 (1H, s).

(x) 1-(2,6-Difluoro-4-trifluoromethyl)-5-chloro-4-trifluoromethylpyrimidin-6-one (compound no 39 in Table 1), except that the reaction mixture was heated to 90° C. for 48 hours.

'H NMR δ(CDCl$_3$) 8.05 (1H, s) and 7.5 (2H, d).

(y) 1-(2-Bromo-6-chloro-4-trifluoromethyl)-4-pentafluoromethylpyrimidin-6-one (compound no 42 in Table 1), except that the reaction mixture was heated to 90° C. for 16 hours. The compound showed m.p. 172°-173° C.

'H NMR δ(CDCl$_3$) 8.00 (2H, brs), 7.88 (1H, s) and 7.08 (1H, s).

(z) 1-(2,6-dibromo-4-trifluoromethyl)-4-pentafluoroethylpyrimidin-6-one (compound no 45 in Table 1) except that the reaction mixture was heated to 90° C. for 16 hours. The compound showed m.p. 175.8°-176.2° C.

'H NMR δ(CDCl$_1$) 8.05 (2H, s), 7.98 (1H, s) and 7.06 (1H, s).

(aa) 1-(2,6-dichloro-4-trifluoromethyl)-5-chloro-4-pentafluoromethylpyrimidin-6-one (compound no 46 in Table 1) except that the reaction mixture was heated to 90° C. for 16 hours.

'H NMR δ(CDCl$_3$) 7.9 (1H, s) and 7.82 (1H, s).

The product was shown by G.L.C. analysis is to contain 10% of 1-(2,6-dichloro-4 -trifluoromethyl-4-pentafluoroethylpyrimidin-6-one as an impurity.

EXAMPLE 3

This Example illustrates an alternative preparation of 1-(2-Chloro-6-nitro-4-trifluoromethylphenyl)-4-trifluoromethylpyrimidin-6-one (Compound 2 in Table I).

A dry reaction flask was purqed with nitrogen and charged with a 50% suspension of sodium hydride (640 mg). The sodium hydride was suspended in DMF (20 .ml). Solid 6-trifluoromethylpyrimidin-6-one (2 g, 12 mmol) was added portionwise, the mixture stirred for a further 10 minutes, and then 3-chloro-4-fluoro-5-nitrobenzotrifluoride (3.3 g) was added in one portion. The deep-red reaction mixture was vigorously stirred for ten minutes and then poured into water and extracted rigorously with ether. The combined ethereal layers were washed with water, then brine, and dried over maqnesium sulphate. The solvent was removed under reduced pressure to afford a yellow residue which was recrystallised from a mixture of ethyl acetate and hexane to qive 1-(2-chloro-6-nitro-4-trifluoromethylphenyl)-4-trifluoromethylpyrimidin-6-one as yellow crystals (2.3 g), mp 149°–150° C., and NMR spectrum as before.

EXAMPLE 4

The following compounds were prepared according to the general method of Example 3 from appropriate compounds of formula II and formula III.

(a) 1-(2,6-Dinitro-4-trifluoromethylphenyl)-4-trifluoromethylpyrimidin-6-one (Compound 3 in Table I) mp 194°–197.6° C.

'H NMR $\delta(CDCl_3)$ 8.82 (2H. s), 8.60 (1H, s), 6.95 (1H, s).

(b) 1-(2-Chloro-4-nitro-4-trifluoromethylphenyl)-5-fluoro-4-trifluoromethylpyrimidin-6-one (Compound 7 in Table I).

'H NMR $\delta(CDCl_3)$: 8.48 (1H, s), 8.24 (1H, s), 7.92 (1H, s).

(c) 1-(2-Chloro-6-nitro-4-trifluoromethylphenyl)-5-bromo-4-trifluoromethylpyrimidin-6-one (Compound 8 in Table I) mp. 141°–142° C.

'H NMR: $\delta(CDCl_3)$: 8.45 (1H, s), 8.20 (2H, s), 8.05 (1H, s).

(d) 1-(2,6-dinitro-4-trifluoromethylphenyl)-5-chloro-4-trifluoromethylpyrimidin-6-one (Compound 24 Table I); except that the reaction mixture was maintained at room temperature for 16 hours. The compound showed mp. 190°–193° C.

'H NMR $\delta(CDCl_3+3$ drops DMSO) 8.85 (2H, s) and 8.60 (1H, s).

(e) 1-(2-chloro-6-nitro4-trifluoromethylphenyl)-5-iodo-4-trifluoromethylpyrimidin-6-one (Compound 14 Table I); except that the reaction mixture was maintained at room temperature for 1 hour. The compound showed mp. 151°–153° C.

'H NMR $\delta(CDCl_3)$ 8.44 (1H fine d), 8.20 (1H, fine d) and 7.98 (1H, s).

(f) 1-(2-chloro-6-nitro-4-trifluoromethylphenyl)-4-chloropyrimidin-6-one (compound 36 in Table I); except that the reaction mixture was maintained at ambient temperature for 2 hours. The compound showed mp. 170.5°–172.1° C.

'H NMR $\delta(CDCl_3)$ 8.40 (1H, s); 8.20 (1H, s), 7.95 (1H, s) and 6.68 (1H, s).

(g) 1-(2-chloro-6-nitro-4-trifluoromethylphenyl)-5-chloro-4-pentafluoroethylpyrimidin-6-one (compound no 37 in Table I); except that the reaction mixture was maintained at room temperature for 2 hours. The compound showed mp. 170°–171.2° C.

'H NMR $\delta(CDCl_3)$ 8.46 (1H, d), 8.22 (1H, d), 8.00 (1H, s).

(h) 1-(2-Chloro-6-nitro-4-trifluoromethylphenyl)-4-difluoromethylpyrimidin-6-one (compound no 41 in Table I); except that the reaction mixture was maintained at ambient temperature for 1.5 hours. The compound showed mp. 130°–132° C.

'H NMR $\delta(CDCl_3)$ 8.41 (1H, d), 8.19 (1H, d), 8.05 (1H, s), 6.90 (1H, s) and 6.47 (1H, t).

(i) 1-(2-Bromo-6-nitro-4-trifluoromethyl)-4-pentafluoroethylpyrimidin-6-one (compound no 44 in Table I); except that the reaction mixture was maintained at ambient temperature for 1 hour. The compound showed m.p. 138°–139° C.

'H NMR $\delta(CDCl_3)$ 8.48 (1H, d), 8.38 (1H, d), 8.10 (1H, s) and 7.02 (1H, s).

EXAMPLE 5

This Example illustrates the preparation of 1-(3-chloro-2,6-dinitro-4-trifluoromethylphenyl)-4-trifluromethylpyrimidin-6-one (Compound 16 in Table I.).

A mixture of 4-trifluoromethylpyrimidin-6-one (0.48 g), 2,4-dichloro-3,5-dinitrotrifluorobenzene (0.9 g) and potassium carbonate (0.41q) in dry dimethylformamide (10 ml) was vigorously stirred at ambient temperature for a period of 15 minutes. The reaction mixture was then poured into water, and extracted into ethyl acetate. After drying and evaporation of the solvent, under reduced pressure, the residue was subjected to chromatography on silica gel using 30% (by volume) ethylacetate in petroleum ether (boiling range 60°–80° C.) as eluent. The required fractions were combined, and the solvent removed under reduced pressure to qive a yellow solid, which was then triturated with petroleum ether (boiling range 60°–80° C.). The solid was dissolved in boiling ethanol, filtered, and the solvent removed under reduced pressure. The residue was again triturated with petroleum ether (boiling range 60°–80° C.) and finally recrystallised from petroleum ether (boiling range 60°–80° C.) containing ethylacetate (9% by volume) to qive 1-(3-chloro-2,6-dinitro-4-trifluoromethylphenyl)-4-trifluoromethylpyrimidin-6-one as a yellow solid:

'H NMR $\delta(CDCl_3)$ 8.8 (1H, s), 8.1 (1H, s) and 6.95 (1H, s).

EXAMPLE 6

This Example illustrates the preparation of 1-(2-Chloro-6-fluoro-4-trifluoromethyl)-5-bromo-4-trifluoromethylpyrimidin-6-one (Compound 19 in Table I).

5-Chloro-3,4-difluorotrifluoromethylbenzene was reacted with 5-bromo-4-trifluoromethylpyrimidin-6-one according to the procedure given in Example 1. The resultant product was then reacted with a mixture of bromine (0.1 eg) and sodium acetate (0.3 eq) in acetic acid for 16 hours. The reaction mixture was then poured into water, and extracted with ethyl acetate. The organic layer was washed with aqueous sodium bicarbonate solution, followed by aqueous sodium thiosulphate solution and finally brine. After drying and filtration, evaporation of the solvent under reduced pressure gave 1-(2-chloro-6-fluoro-4-trifluoromethyl)-5-bromo-4-trifluoromethylpyrimidin6-one as a pale orange solid mp. 122°–125° C.

'H NMR $\delta(CDCl_3)$ 8.00 (1H, s); 7.74 (1H, s) and 7.55 (1H, d).

EXAMPLE 7

This Example illustrates the preparation of 1-(2,6-difluoro-4-trifluoromethylphenyl)-5-bromo-4-trifluoromethylpyrimidin-6-one (compound 23 in Table I).

A solution of bromine (146 mg) in acetic acid (1 ml) was added dropwise to a solution of compound 11 (in Table I) (285 mg) and sodium acetate (204 mg) in acetic acid (3 ml). After stirring at the ambient temperature for 16 hours, the solvent was removed by evaporation under reduced pressure and the residue dissolved in aqueous sodium bicarbonate solution. After extraction with ethyl acetate, the organic layer was washed with aqueous sodium thiosulphate solution, dried and filtered, and concentrated under reduced pressure to qive a pale yellow solid. Recrystallization from a mixture of ethyl acetate and petroleum ether (boiling range 60°–80° C.) gave 1-(2,6-difluoro-4-trifluoromethylphenyl)-5-bromo-4-trifluoromethylpyrimidin-6-one;

'H NMR $\delta(CDCl_3)$ 8.05 (1H, s) and 7.48 (2H, d).

EXAMPLE 8

The following compounds were prepared according to the general method of Example 7 from the appropriate compounds of formula I.

(a) 1-(2-bromo-6-nitro-4-trifluoromethyl)-5-bromo-4-trifluoromethylpyrimidin-6-one (Compound 26 in Table I). The compound showed mp. 139°–141° C.

'H NMR $\delta(CDCl_3)$ 8.50 (1H, m), 8.38 (1H, m) and 8.02 (1H, m).

b) 1-(2,6-Dichloro-4-trifluoromethyl)-5-bromo-4-pentafluoroethylpyrimidin-6-one (Compound 33 in Table I). The compound showed mp. 140.5°–141.5° C.

'H NMR $\delta(CDCl_3)$ 7.92 (1H, s) and 7.83 (2H, s).

(c) 1-(2-Chloro-6-fluoro-4-trifluoromethyl)-5-bromo-4-pentafluoroethylpyrimidin-6-one (compound no 40 in Table I). The compound showed mp. 94°–96° C.

'H NMR $\delta(CDCl_3)$ 8.00 (1H, s), 7.78 (1H, s) and 7.58 (1H, d).

(d) 1-(2-Chloro-6-bromo-4-trifluoromethyl)-5-bromo-4-pentafluoroethylpyrimidin-6-one (compound no 43 in Table I). The compound showed mp. 148.5°–149.5° C.

'H NMR $\delta(CDCl_3)$ 7.99 (1H, d), 7.90 (1H, s) and 7.87 (1H, d).

(e) 1-(2,6-dibromo-4-trifluoromethyl)-5-bromo-4-pentafluoroethylpyrimidin-6-one (compound no 47 in Table I). The compound showed mp. 158°–159.5° C.

'H NMR $\delta(CDCl_3)$ 8.02 (2H, s) and 7.90 (1H, s).

(f) 1-(2,6-Dibromo-4-trifluoromethyl)-5-bromo-4-trifluoromethylpyrimidin-6-one (compound 34 in Table I). The compound showed mp 163.5°–164.5° C.

'H NMR $\delta(CDCl_3)$ 8.03 (2H, s), 7.92 (1H, s).

EXAMPLE 9

The following compound was prepared according to the general method of Example 6 from the appropriate compounds.

(a) 1-(2-Chloro-6-nitro-4-trifluoromethyl)-5-bromo-4-pentafluoroethylpyrimidin-6-one (Compound 29 in Table I). The compound showed mp. 178°–181° C.

'H NMR $\delta(CDCl_3)$ 8.46 (1H, d), 8.21 (1H, d) and 8.02 (1H, s).

EXAMPLE 10

This Example illustrates the insecticidal properties of the compounds of formula (I).

The activity of the compounds was determined using a variety of insect pests. The compound was used in the form of liquid preparations containing 500 parts per million (ppm) by weight of the compound. The preparations were made by dissolving compound the in acetone and diluting the solutions water with containing 0.01% by weight of a wetting sold agentunder the trade name "SYNPERONIC" NX until liquid the preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table II for the compounds, at the rate in parts per million given in the second column as a grading of mortality designated as 9, 5 or 0 wherein 9 indicates 80–100% mortality, 5 indicates 50–79% mortality and 0 indicates less than 50% mortality.

In Table III the pest organism used is designated by a letter code and the pest species, the support medium or food, and the type and duration of test is given.

In similar tests, certain compounds of formula (I) showed activity against *Nephotettix Cincticeps* (green leaf hopper-nymphs), *Spodoptera exicua* (lesser army worm-larvae) and *Heliothis virescens* (tobacco budworm-larvae).

TABLE II

| COMPOUND | RATE OF APPLICATION ppm | SPECIES MD (see Table III) | SPECIES BG (see Table III) |
|---|---|---|---|
| 1 | 500 | 9 | 9 |
| 2 | 500 | 9 | 9 |
| 4 | 500 | 9 | 9 |
| 5 | 500 | 9 | 9 |
| 6 | 500 | 9 | 9 |
| 8 | 500 | 0 | 5 |
| 9 | 500 | 5 | 9 |
| 10 | 500 | 9 | 9 |
| 11 | 500 | 9 | 9 |
| 12 | 500 | 0 | 9 |
| 13 | 500 | 9 | 9 |
| 14 | 500 | 9 | 9 |
| 15 | 500 | 5 | 0 |
| 17 | 500 | 9 | 9 |
| 18 | 500 | 9 | 9 |
| 19 | 500 | 9 | 9 |
| 20 | 500 | 9 | 9 |
| 21 | 500 | 9 | 9 |
| 22 | 500 | 9 | 9 |
| 23 | 500 | 0 | 9 |
| 25 | 500 | 5 | 9 |
| 26 | 500 | 9 | 5 |
| 27 | 500 | 9 | 9 |
| 28 | 500 | 9 | 9 |
| 29 | 500 | 0 | 5 |
| 30 | 500 | 0 | 9 |
| 31 | 500 | 0 | 9 |
| 32 | 500 | 0 | 9 |
| 33 | 500 | 0 | 9 |
| 34 | 500 | 0 | 9 |
| 37 | 500 | 9 | 9 |
| 38 | 500 | 9 | 9 |
| 39 | 500 | 9 | 9 |
| 40 | 500 | 9 | 9 |
| 41 | 500 | 9 | 0 |
| 42 | 500 | 9 | 9 |
| 43 | 500 | 9 | 9 |
| 44 | 500 | 9 | 9 |
| 45 | 500 | 9 | 9 |
| 46 | 500 | 9 | 9 |
| 47 | 500 | 9 | 9 |

A dash indicates not tested.

TABLE III

| CODE LETTERS (Table II) | TEST SPECIES | SUPPORT MEDIUM/ FOOD | TYPE OF TEST | DURATION (Days) |
|---|---|---|---|---|
| BG | *Blattella germanica* | Plastic pot | Residual | 3 |

TABLE III-continued

| CODE LETTERS (Table II) | SUPPORT TEST SPECIES | MEDIUM/ FOOD | TYPE OF TEST | DURA- TION (Days) |
|---|---|---|---|---|
| | (Cockroach nymphs) | | | |
| MD | *Musca domestica* (houseflies - adults) | Cotton wool/ sugar | Contact | 1 |

"Contact" test indicates that both pests and medium were treated and "Residual" indicates that the medium was treated before infestation with the pests.

What is claimed is:

1. A pyrimidinone compound of formula (IIIA) or (VA):

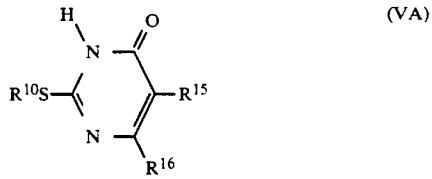

wherein $R^{13}$ is hydrogen or halogen and $R^{14}$ is trifluoromethyl or pentafluoroethyl, with the proviso that when $R^{14}$ is trifluoromethyl, $R^{13}$ is halogen;

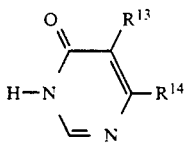

wherein $R^{10}$ is hydrogen or $C_{1-4}$alkyl; $R^{15}$ is cyano and $R^{16}$ is trifluoromethyl, difluoromethyl or pentafluoroethyl or $R^{15}$ is hydrogen or halogen other than fluorine and $R^{16}$ is pentafluoroethyl or difluoromethyl.

2. A compound according to claim 1 of formula (VA).

3. A compound according to claim 1 of formula (IIIA).

* * * * *